United States Patent
Cunningham et al.

(10) Patent No.: US 8,646,164 B2
(45) Date of Patent: Feb. 11, 2014

(54) AUTOMATED ASSEMBLY DEVICE TO TOLERATE BLADE VARIATION

(75) Inventors: James S. Cunningham, Boulder, CO (US); James J. Crawford, Lyons, CO (US); Paul Guerra, Los Gatos, CA (US)

(73) Assignee: Covidien LP, Mansfield, MA (US)

( * ) Notice: Subject to any disclaimer, the term of this patent is extended or adjusted under 35 U.S.C. 154(b) by 1099 days.

(21) Appl. No.: 12/414,346

(22) Filed: Mar. 30, 2009

(65) Prior Publication Data

US 2009/0248052 A1 Oct. 1, 2009

Related U.S. Application Data

(60) Provisional application No. 61/041,130, filed on Mar. 31, 2008.

(51) Int. Cl.
*B23Q 3/00* (2006.01)

(52) U.S. Cl.
USPC .......................................................... 29/468

(58) Field of Classification Search
USPC .................................................. 29/468, 428
See application file for complete search history.

(56) References Cited

U.S. PATENT DOCUMENTS

| | | | |
|---|---|---|---|
| 4,074,431 A | 2/1978 | Beaver et al. |
| 4,122,856 A | 10/1978 | Mosior et al. |
| 4,385,692 A | 5/1983 | Eldridge, Jr. |
| 4,543,857 A | 10/1985 | Kleinberg et al. |
| 5,382,255 A | 1/1995 | Castro et al. |
| 5,433,321 A | 7/1995 | Abidin et al. |
| 5,657,541 A | 8/1997 | Hickok et al. |
| 5,981,895 A | 11/1999 | Grace et al. |
| 6,742,236 B1 | 6/2004 | Dion et al. |
| 7,155,795 B2 | 1/2007 | Abidin et al. |
| 2003/0229344 A1 | 12/2003 | Dycus et al. |
| 2007/0062017 A1 | 3/2007 | Dycus et al. |

*Primary Examiner* — David Bryant
*Assistant Examiner* — Moshe Wilensky

(57) ABSTRACT

An automated device facilitates the assembly a surgical instrument that includes a knife with a high aspect ratio. The automated device includes a fixture for restraining a subassembly of the surgical instrument that includes the knife. A blade grip on the device is movable relative to the fixture, and is configured to urge the knife into a restrained position in the subassembly suitable for the subsequent assembly of an additional instrument component. A grip actuator is provided to move the blade grip.

3 Claims, 16 Drawing Sheets

AUTOMATED ASSEMBLY DEVICE TO TOLERATE BLADE VARIATION

CROSS-REFERENCE TO RELATED APPLICATIONS

This application claims the benefit of priority to U.S. Provisional Application Ser. No. 61/041,130 entitled "AUTOMATED ASSEMBLY DEVICE TO TOLERATE BLADE VARIATION" filed Mar. 31, 2008 by Jim Cunningham et al, which is incorporated by reference herein.

BACKGROUND

1. Technical Field

The present disclosure relates to a device for assembling a surgical instrument. In particular, the device automates certain steps of an assembly process to ensure components of the instrument are properly aligned and connected.

2. Background of Related Art

Many surgical instruments include a blade or knife for mechanical tissue cutting. Often these knives are positioned at a distal end of the instrument and are operable from a proximal location on the instrument to traverse a particular path through the tissue. This arrangement may be particularly evident in surgical instruments configured for minimally invasive surgery. In a minimally invasive surgical procedure, a narrow tube or cannula may be inserted through a small incision made in a patient to provide access to a surgical site. Surgical instruments configured for minimally invasive surgery are thus typically equipped with an elongate shaft coupling a working head at the proximal end of the instrument to the end effector at the distal end of the instrument. The knife typically forms a component of the end effector, and control surfaces for activating the knife are typically located on the working head. Positioning the elongate shaft through the cannula thus permits a surgeon to manipulate the knife at an internal surgical site from the control surfaces that remain on the exterior of the patient.

To facilitate this remote operability, an aspect ratio of the knife may be relatively high, i.e., the geometry of the knife may be long and narrow. A knife exhibiting a long and narrow geometry may tend to bend, warp or otherwise deviate from a flat or straight configuration. These deviations may be relatively random such that each knife manufactured to a particular specification is distinct from other such knives, and these distinctions may present difficulties in defining an assembly procedure for instruments including the knives.

Typically, a knife may be manually assembled with other instrument components such as a support structure or knife guide. The knife guide may have an opening configured to receive the knife such that the knife may be visually aligned and threaded through the opening. The knife guide may be subsequently assembled into the instrument with the knife protruding from the opening. Such a process is labor intensive and presents various opportunities for error and damage to the instrument components. For example, a manually assembled knife could be damaged by unintended contact with the knife guide. Accordingly, the assembly of a surgical instrument may be facilitated by an assembly device that automates certain steps of the assembly process while accounting for variations in blade geometry.

SUMMARY

The present disclosure describes an automated device, which may facilitate the assembly a surgical instrument that employs a knife with a high aspect ratio. The automated device includes a fixture for restraining a subassembly of the surgical instrument that includes a knife. A blade grip on the device is movable relative to the fixture, and is configured to urge the knife into a restrained position in the subassembly suitable for the subsequent assembly of an additional instrument component. A grip actuator is provided to move the blade grip.

The grip actuator may be configured to move the blade grip in a lateral direction relative to the subassembly, and the device may further comprise at least one tapered finger extending in the lateral direction, such that a leading portion of the tapered finger encounters the knife in an unrestrained position and a trailing portion of the tapered finger encounters the knife in the restrained position. The blade grip may be configured to urge the knife toward the restrained position in a vertical direction relative to the subassembly, and the grip actuator may include a pneumatic slide.

The device may further include a component block configured to restrain the additional assembly component, and the component block may be moveable in a longitudinal direction relative to the fixture to approximate the additional assembly component and the subassembly. The device may also include a knife block configured to move relative to the fixture to define a longitudinal position of the knife within the subassembly.

According to another aspect of the disclosure, a device for facilitating the assembly of a surgical instrument may include a fixture for restraining a subassembly of the surgical instrument including a knife, a knife block moveable in a longitudinal direction relative to the fixture to define a longitudinal position of the knife within the subassembly, and a component block configured to restrain an additional assembly component. The knife block and the component block may be configured for concurrent movement to facilitate assembly of the additional assembly component to the subassembly.

The knife block and the component block may also be selectively configured for selective independent movement relative to one another. The device may include a blade grip, which is moveable in a lateral direction to define a vertical position of the knife within the subassembly. The device may further include a jaw block for restraining a jaw member to be installed onto the subassembly, the jaw block mountable relative to the fixture such that the jaw member operably engages the knife upon movement of the knife block.

According to still another aspect of the disclosure, a method of assembling a surgical instrument including a knife includes may include loading a subassembly of the instrument that includes the knife into a fixture such that the knife is movable within the subassembly, advancing a blade grip to urge the knife to a restrained position within the subassembly, approximating an additional instrument component relative to the subassembly to constrain the additional instrument component within the subassembly, and moving the instrument component and the knife concurrently to install the additional instrument component.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION

Figure 1:
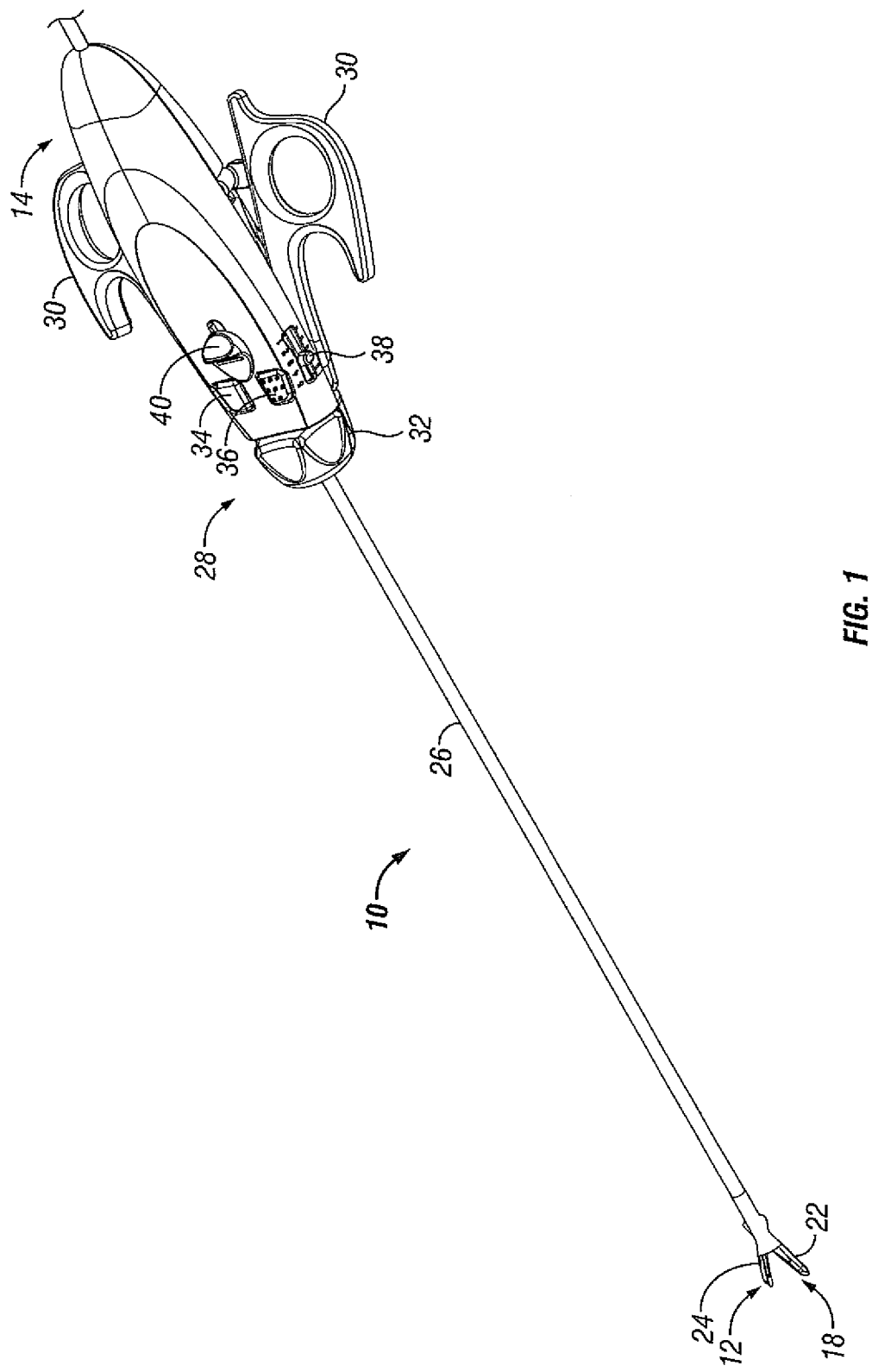
FIG. 1 is an perspective view of a surgical instrument that may be assembled by the processes and devices described herein.

The devices and processes of the present disclosure may facilitate accurate assembly of a surgical instrument such as an electrosurgical forceps 10. A more detailed description of the assembly and operation of forceps 10 may be found in commonly assigned U.S. Patent Application Publication No. 2007/0078456 to Dumbauld et al. The attached figures illustrate exemplary embodiments of the present disclosure and are referenced to describe the embodiments depicted therein. Hereinafter, the disclosure will be described in detail by explaining the figures wherein like reference numerals represent like parts throughout the several views Referring initially to FIG. 1, the electrosurgical forceps 10 includes a distal end 12 and a proximal end 14. An end effector 18 near the distal end 12 is configured to manipulate tissue at a surgical site by clamping, electrosurgically energizing, cutting and/or otherwise contacting the tissue. Two jaw members 22, 24 of the end effector 18 are configured to move between an open position as shown in FIG. 1, in which the distal-most ends are substantially spaced and a closed position wherein the distal most ends are closer together. The end effector 18 is coupled to an elongate shaft 26. Elongate shaft 26 facilitates the use of forceps 10 in a minimally invasive surgical procedure, wherein the elongate shaft 26 is inserted through a cannula as discussed above. At the proximal end of forceps 10 is a working head 28 including several control surfaces, which a surgeon uses to remotely manipulate the end effector 18. For example, handles 30 may be drawn together to approximate jaws 22, 24 or drawn apart to separate jaws 22, 24. Other control surfaces may include a knob 32, which may be used to rotate the end effector 18, buttons 34, 36, which may be used to initiate various modes electrosurgical energy delivery to the jaws 22, 24, a slide 38, which may be used to control the intensity of electrosurgical energy delivered, and trigger 40, which may be used to advance a knife 42 (FIG. 2A) through tissue clamped by jaws 22, 24.

Figure 2A:
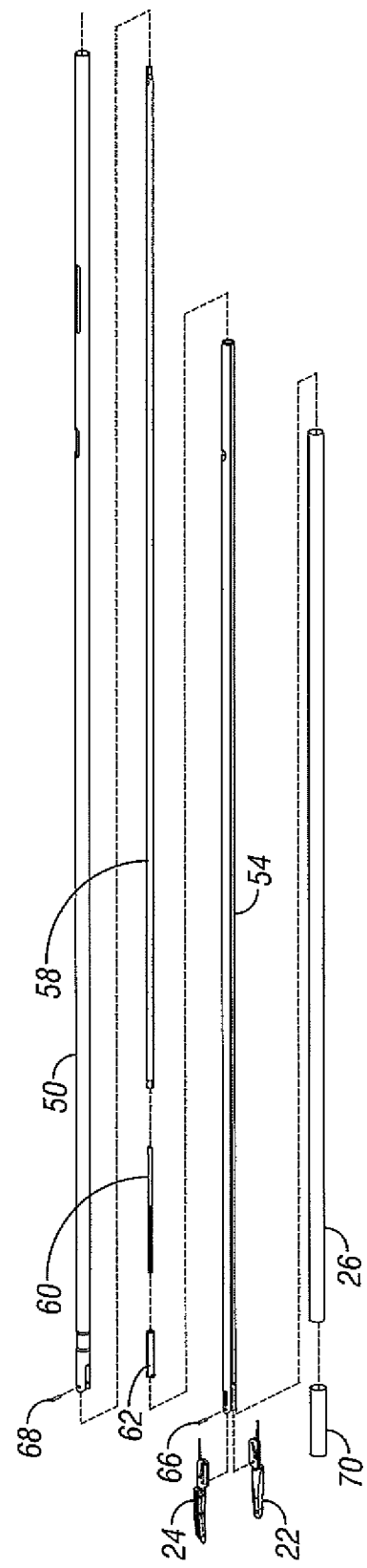
FIG. 2A is an exploded, perspective view of a distal portion of the instrument of FIG. 1 including a knife having a long and narrow geometry and a knife guide for affecting movement of the knife.

Referring now to FIG. 2A, an arrangement of a distal portion of forceps assembly 10 is described that permits a surgeon to operate end effector 18 from the proximal end 14 of the forceps 10. Within elongate shaft 26, several components are arranged in a generally concentric relation and moveable relative to one another in order to transmit motion from the proximal end 14 to the end effector 18. For example, a drive sleeve 50 is received within elongate shaft 26 in a manner permitting the drive sleeve 50 to longitudinally translate or reciprocate relative to the elongate shaft 26. A rotating shaft 54 is similarly received within the drive sleeve 50 such that the drive sleeve 50 may reciprocate relative to the rotating shaft 54. A knife bar 58 is received within the rotating shaft 54 such that the knife bar 58 may reciprocate relative to the rotating shaft 54. A knife 60 is coupled to a distal end of the knife bar 58, such that the knife 60 reciprocates along with the knife bar 58. The knife 60 may be attached to the knife bar 58 in any suitable way, e.g., snap-fit, fiction-fit, pinned, welded, glued, etc.

A knife guide 62 is supported in the rotating shaft 54 and remains stationary with respect to the rotating shaft 54. Knife guide 62 may be press fit into an opening in the distal end of the rotating shaft 54 and includes a tapered interior channel therein (see FIG. 9C) to receive knife 60. The knife guide may thus urge knife 60 into a central position within the rotating shaft 54 and ensure proper alignment of knife 60 as it reciprocates within upper and lower jaw members 22, 24 (see FIG. 2D). Knife guide 62 may also serve to protect the knife 60 and other components from damage throughout the assembly process as will be described in greater detail below.

A pivot pin 66 and a drive pin 68 are included to operatively associate the upper and lower jaws 22, 24 to both drive sleeve 50 and rotating shaft 54. An insulating boot 70 is positioned over a distal end of the drive sleeve 50 and a portion of upper and lower jaws 22, 24. The boot 70 may be formed from a flexible or resilient material such that the boot 70 may accommodate the movement of upper and lower jaws 22, 24 as the jaws are approximated and separated.

Figure 2B:
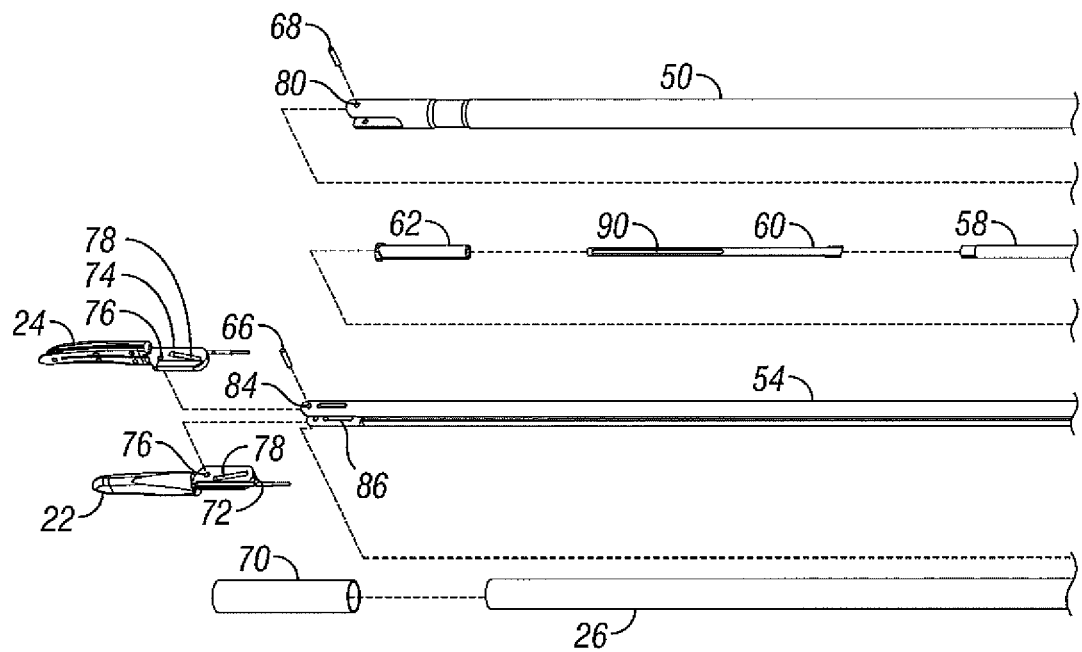
FIG. 2B is a close up view of the end effector of FIG. 2A.

Referring now to FIG. 2B, jaw member 22 is equipped with a proximal flange 72 and jaw member 24 is equipped with a proximal flange 74. Each of the proximal flanges 72, 74 includes a pivot hole 76 to receive pivot pin 66 and a drive slot 78 to receive drive pin 68 therein. The pivot hole 76 and the drive slot 78 are configured to permit appropriate relative motion of the jaw members 22, 24 about the pivot pin 66 and drive pin 68. Drive sleeve 50 and rotating shaft 54 are each equipped with a bifurcated distal end to accommodate the proximal flanges 72, 74 of jaw members 22, 24. Drive sleeve 50 includes a bore 80 extending through both portions of its bifurcated end, and similarly, rotating shaft 54 includes a bore 84 extending through both portions of its bifurcated end. Bores 80, 84 are configured to fixedly retain respective pins 66, 68 therein by a press-fit or similar connection. Rotating shaft 54 also includes a longitudinal slot 86 extending through both portions of its bifurcated end. Longitudinal slot 86 is configured to accommodate longitudinal movement of drive pin 68 there through. Knife 60 also includes an elongate slot 90 that permits knife 60 to reciprocate without interfering with pins 66, 68.

Figure 2C:
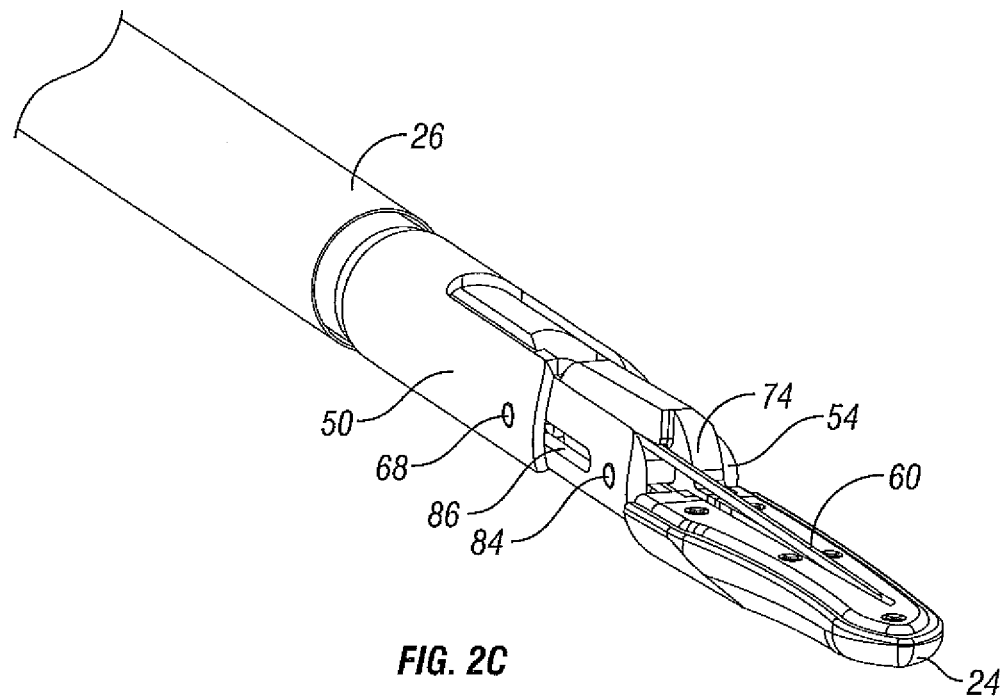
FIG. 2C is a partial, perspective view of the end effector of FIG. 2B in an assembled and closed configuration depicting the knife in an extended position.
Figure 2D:
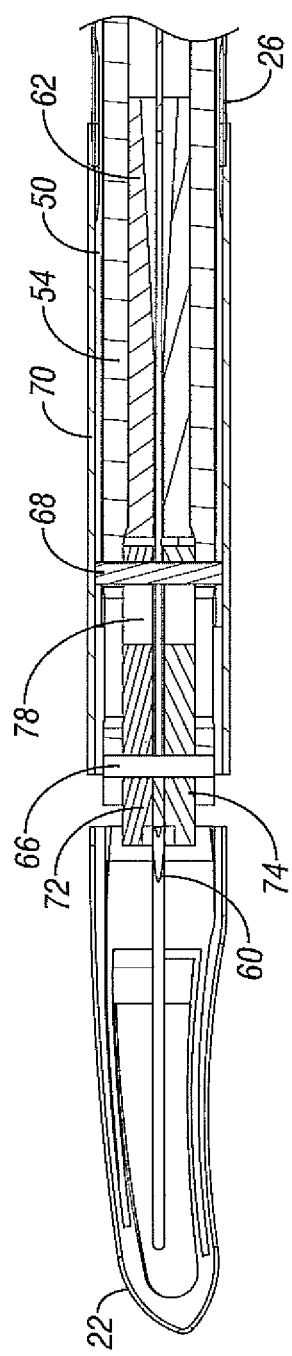
FIG. 2D is a top, cross-sectional view of the end effector of FIG. 2C depicting the knife in a retracted position.
Figure 2E:
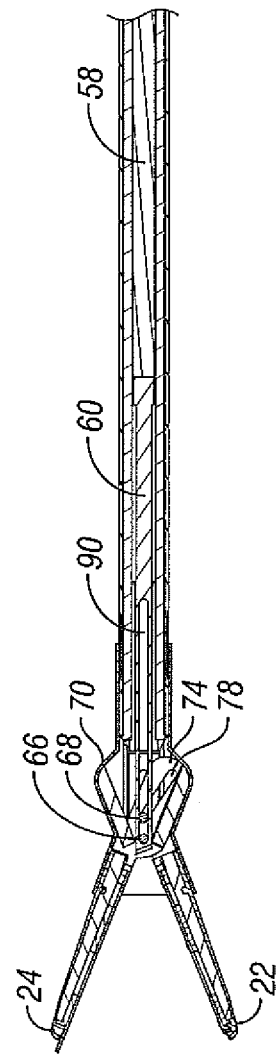
FIG. 2E is a side, cross-sectional view of the end effector of FIG. 2D in an open configuration.

When fully assembled, pivot pin 66 is positioned through bore 84, pivot holes 76 and elongate slot 90 to permit the jaw members to pivot about the pivot pin 66. Drive pin 68 is positioned through bore 80, longitudinal slot 86, drive slots 78, and elongate slot 90. As depicted in FIGS. 2C and 2D, this arrangement provides for a closed configuration of jaw members 22, 24 (jaw member 22 and boot 70 are removed for clarity) in which drive slots 78 are oriented in general alignment with a longitudinal axis of the instrument 10. When jaw members 22, 24 are in the closed configuration, drive pin 68 is disposed in a proximal position within the drive slots 78 and within longitudinal slot 86. If the drive sleeve 50 is caused to move in a distal direction with respect to the rotating shaft 54, drive pin 68 moves distally within the drive slots 78 toward pivot pin 66. This motion causes the drive slots 78 to move to an oblique orientation out of the general alignment with the longitudinal axis of the instrument 10. Thus jaw members 22, 24 are moved into an open configuration as depicted in FIG. 2E. In this open configuration, drive pin 68 assumes a distal position within the drive slots 78. Imparting an opposite relative motion between drive sleeve 50 and rotating shaft 54, i.e., moving drive sleeve 50 proximally, when the jaw members 22, 24 are in the open configuration serves to move the jaw members to the closed configuration. Handles 30 are configured such that manipulation of the handles 30 effects relative motion between the drive sleeve 50 and rotating shaft 54 to move jaw members 22, 24 between the open and closed configurations.

If knife bar 58 is caused to move distally with respect to the rotating shaft 54, knife 60 is advanced into the jaw members 22, 24 as depicted in FIG. 2C. Elongated slot 90 in the knife 60 permits this motion without interference from pins 66, 68. Trigger 40 is configured such that manipulation of the trigger 40 effects motion of the knife bar 58 to effect advancement of the knife 60.

As can be appreciated, the functionality of instrument components described above may require an intricate assembly process. Each of the instrument components must be properly positioned and oriented in a manner appropriate for a particular step in the assembly process. Such a process may be difficult to accomplish manually as access to a particular instrument component may be limited once the component is installed. Also, any variations in the knife 60 from an entirely straight and flat configuration may further complicate the assembly process. Accordingly, an automated assembly device may facilitate the assembly of the electrical forceps 10 and other instruments that require complicated assembly of components, e.g., a surgical stapler.

Figure 3:
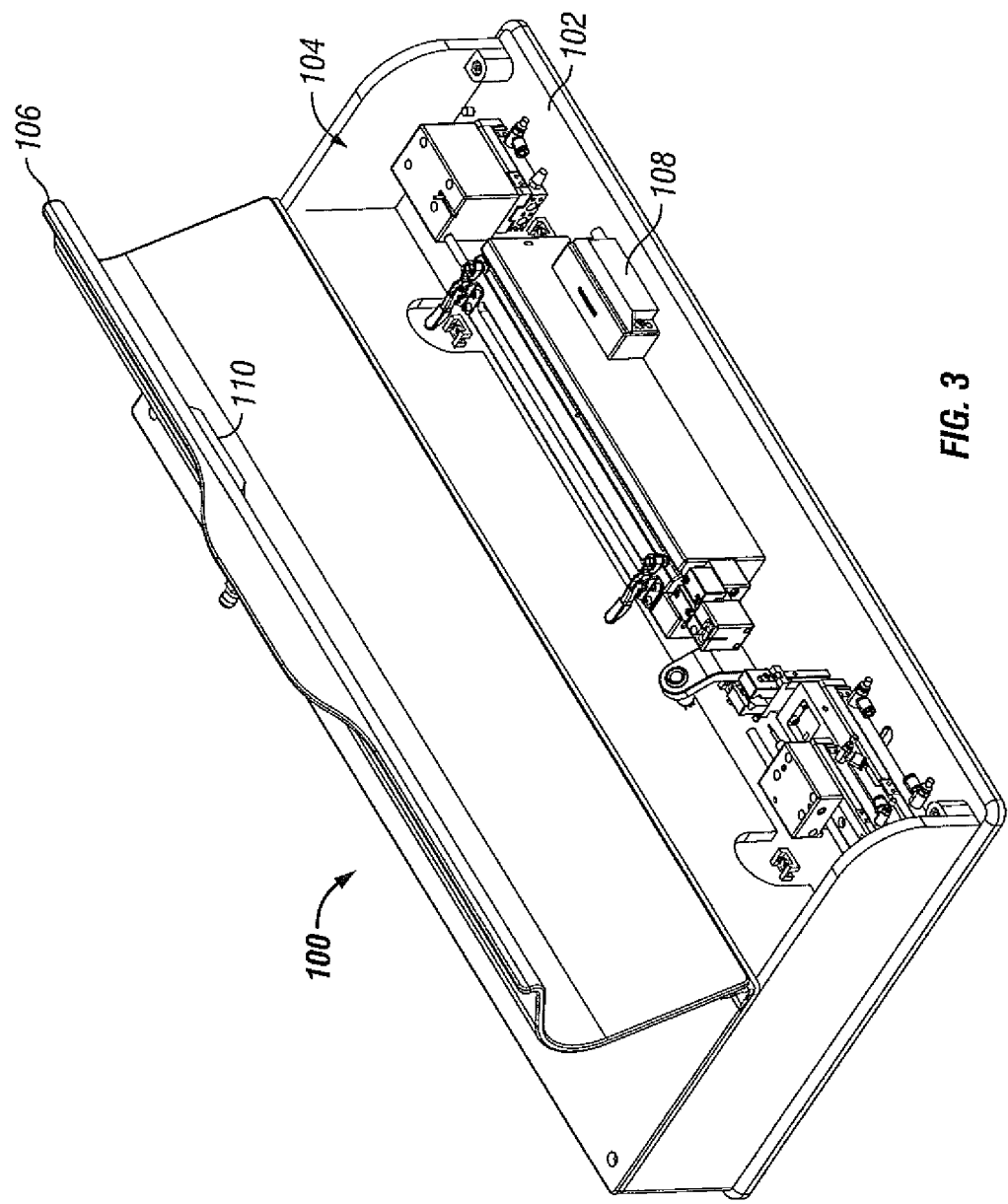
FIG. 3 is a perspective view of an assembly device in accordance with one embodiment of the present disclosure.

Referring now to FIG. 3, an automated assembly device in accordance with the present disclosure is depicted generally as 100. Assembly device 100 includes a base plate 102, that may be configured to be placed on a table-top or other structure to provide an operator convenient access to a forward interior region 104 of the device 100. A hinged safety cover 106 is provided to selectively enclose the forward interior region 104, and to protect the operator during various stages of an assembly process in which automated movement occurs. An interlock 108 is mounted within the forward interior region 104 such that a key 110 mounted on the safety cover 106 is approximate to the interlock 108 when safety cover 106 is in a closed configuration (not shown). A controller (not shown) is included and configured to permit automated movement when safety cover 106 is in a closed configuration, and disable automated movement when safety cover 106 is in an open configuration. Thus, the operator may safely load, unload and manipulate instrument components when safety cover 106 is open.

Figure 4:
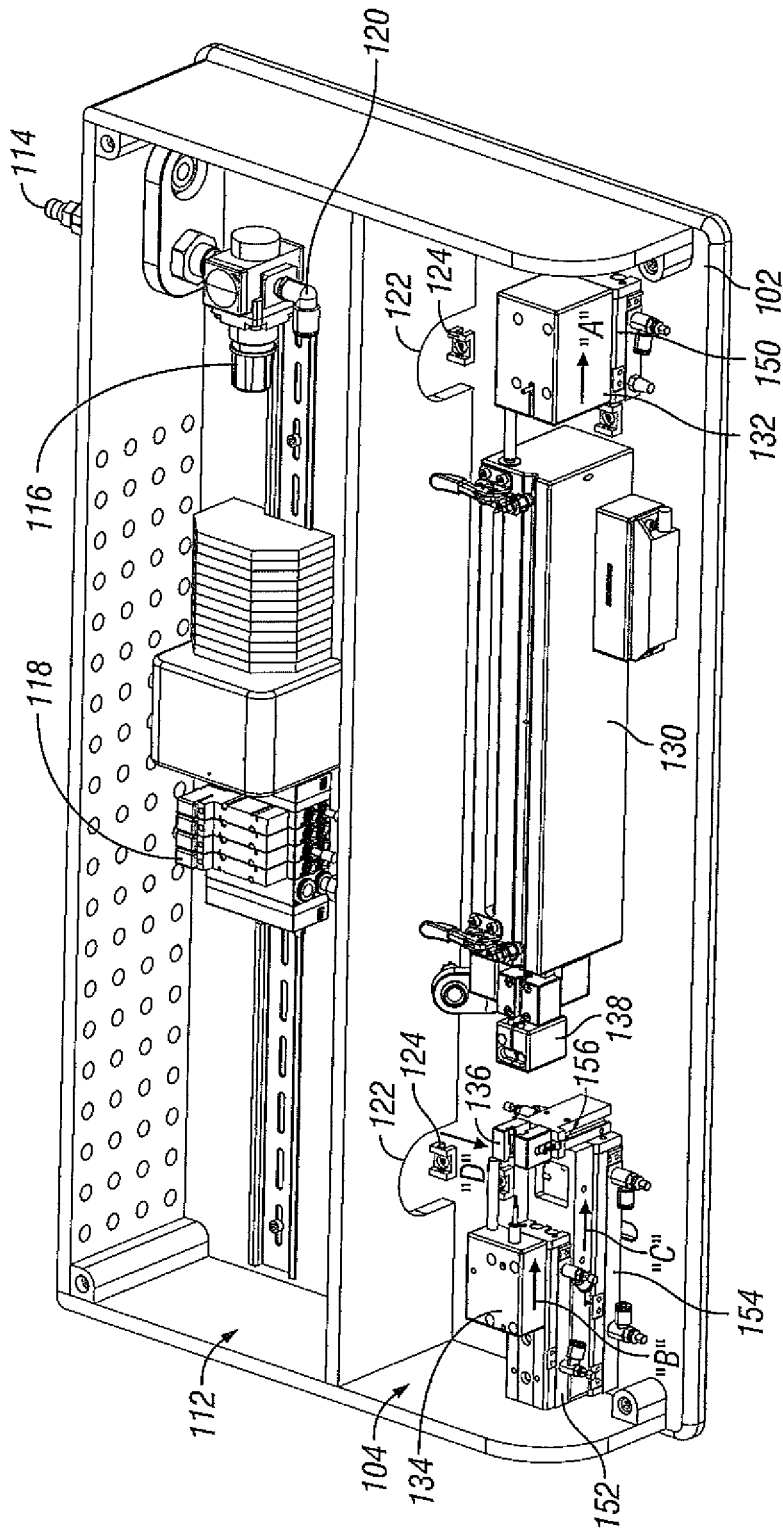
FIG. 4 is a perspective view of the assembly device of FIG. 3 having a safety cover removed to reveal forward and rear interior regions of the assembly device.

Removing safety cover 106 reveals a rear interior region 112 of the assembly device 100 as depicted in FIG. 4. A quick-disconnect coupling 114 provides a pneumatic input for compressed air provided by an external source to enter device components housed in the rear interior region 112. For example, coupling 114 may communicate with device components such as an air pressure regulator 116 or valve bank 118. Components of the assembly device, to which access less frequently required, may be housed in the rear interior region 112. Regulator 116, for example, may require adjustment only once to provide a suitable air pressure for the assembly device 100, and thereafter many forceps 10 or other instruments may be assembled using the device 100.

Extending from regulator 116 is a pneumatic fitting 120. Pneumatic fittings 120 or similar fittings are operatively connected to fluid conduits (not shown) to provide fluid communication between components of assembly device 100. Such fluid conduits are used to deliver compressed air to the forward interior region 104 of the device 110 through either one of gates 122. Gates 122 are equipped with tie-down anchors 124 attached to the base plate to facilitate organization of the fluid conduits. Tie down anchors 124 may be located at various locations throughout the assembly device 100 and provide an opening through which a cable tie or other restraint may be secured.

The forward interior region 104 houses four main device components or assembly blocks, which are used to restrain or manipulate instrument components within the assembly device 100. These include a fixture 130, a knife block 132, a component block 134, and guide block 136. A fifth device component, jaw block 138, is removable from the assembly device 100 to conveniently load smaller instrument components such as jaw members 22, 24 as described in greater detail below.

The four main assembly blocks 130, 132, 134, 136 are arranged as depicted in FIG. 4 to define an initial configuration wherein each assembly block is located in an initial position with respect to the base plate 102. Fixture 130 is centrally located within the forward interior region 104 and is fixedly mounted to the base plate 102. Knife block 132 is mounted to an actuator or carrier component such as precision pneumatic slide 150. Pneumatic slide 150 is configured to selectively advance knife block 132 from an initial position in a longitudinal direction with respect to fixture 130 as indicated by arrow "A." Pneumatic slide 150 may be retracted to return knife block 132 to an initial position. Component block 134 is mounted to pneumatic slide 152, and pneumatic slide 152 is mounted to pneumatic slide 154. Pneumatic slide 152 is configured to selectively advance component block 134 in a longitudinal direction with respect to pneumatic slide 154 as indicated by arrow "B." Pneumatic slide 154 is configured to selectively carry component block 134, pneumatic slide 152, and a guide block 136 together in a longitudinal direction with respect to the base plate 102 as indicated by arrow "C." Guide block 136 is mounted to a pneumatic slide 156, which is configured to selectively carry guide block 136 in a lateral direction with respect to the base plate 102 as indicated by arrow "D." Each of the pneumatic slides 150, 152, 154, and 156 are also configured to selectively return the assembly blocks 130, 132, 134, 136 to respective initial positions.

Figure 5:
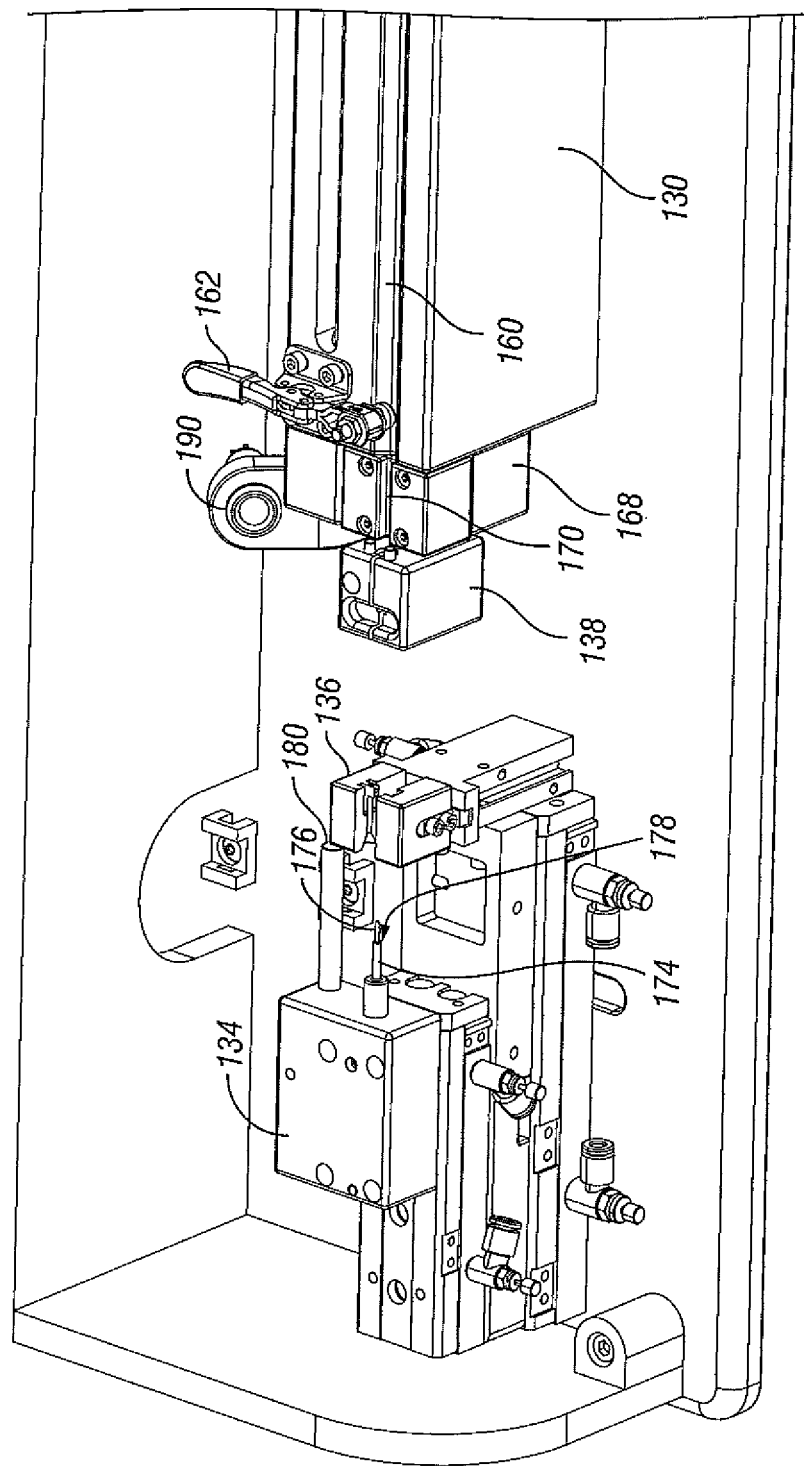
FIG. 5 is a close up, perspective view of a portion of the forward interior region.

Referring now to FIG. 5, fixture 130 includes a shaft reception channel 160 across a top surface thereof. Shaft reception channel 160 is configured to receive a slender instrument component such as rotating shaft 54 therein, and a pair of toggle clamps 162 is provided to secure the instrument component within the channel 160. A sensor housing 168 is disposed on an end of fixture 130 such that a narrow channel 170 across a top surface thereof may receive a distal portion of the instrument component. Narrow channel 170 is in general alignment with channel 160, and is adjustable to precisely define the location of the distal end of the instrument. Sensor housing 168 supports jaw block 138 in a releasable manner on an end opposite of channel 160, and houses a sensor 172 (FIG. 9C), which is configured to detect the presence of jaw block 138 as described in greater detail below.

Component block 134 includes a guide mount 174 projecting therefrom upon which the knife guide 62 may be mounted. The guide mount 174 includes a thin tongue 176 configured to extend into an interior region of the knife guide 62 in order to support the knife guide 62 thereon. A leading face 178 of the guide mount 174 provides a stop for mounting knife guide 62 and leading face 178 enables the guide mount 174 to press the knife guide 62 into position within the rotating shaft 54 upon longitudinal translation of component block 134 during an assembly process described below.

Component block 134 also includes a bumper post 180, which limits the travel distance of component block 134. Bumper post 180 extends from component block 134 in the direction of fixture 130 to define a minimum distance therebetween. Alternatively, bumper post 180 may extend from fixture 130 in the direction of component block 134.

Guide block 136 is bifurcated including two complementary components. At least one of the components of assembly block 136 includes a blade grip 182 (see FIG. 8A) that supports the knife 42 during an assembly process described below. Blade grip 182 may be configured to accommodate blade deviations or variances to facilitate the assembly process.

Also visible in FIG. 5 is a control surface 190. Control surface 190 may take the form of a push button, and may be electrically coupled to the controller (not shown) to perform a variety of functions. For example, control surface 190 may be configured to advance and retract guide block 136, or alternatively provide an emergency stop for the assembly device 100.

Figure 6:
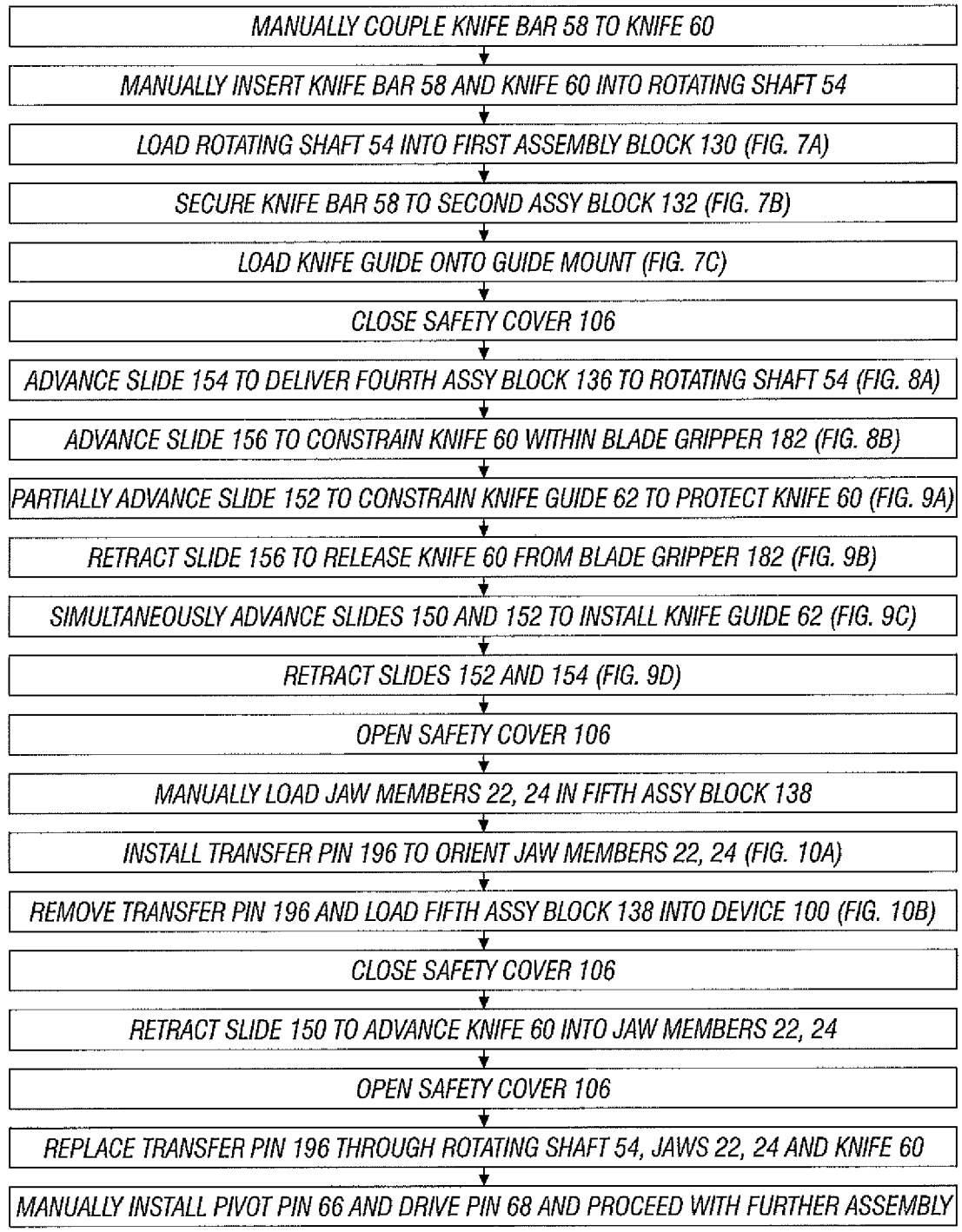
FIG. 6 is a flow chart summarizing a method for assembling the instrument of FIG. 1 using the assembly device of FIG. 3.

Referring now to FIG. 6, an assembly process for the distal end of forceps 10 is summarized in which certain steps are automated to account for variations or deviations in knife 60. An initial preparatory step, which precedes the process outlined in FIG. 6, may be to manually remove jaw block 138 and retain the jaw block 138 for use in later assembly steps. Many of the other steps summarized in FIG. 6 are described in greater detail below with reference to FIGS. 7A though 10C.

An initial assembly step is to manually preassemble some of the instrument components before loading into the forward interior region 104 of assembly device 100. For example, the knife 42 may be fixedly preassembled to knife bar 58 by pinning, welding or any other appropriate means. Once the knife 60 is coupled to the knife bar 58, the knife bar 58 is manually inserted into the rotating shaft 54 in a manner permitting longitudinal translation there between as described above. A subassembly of instrument components is thus be defined by this arrangement of the knife 60, knife bar 58, and rotating shaft 54.

Figure 7A:
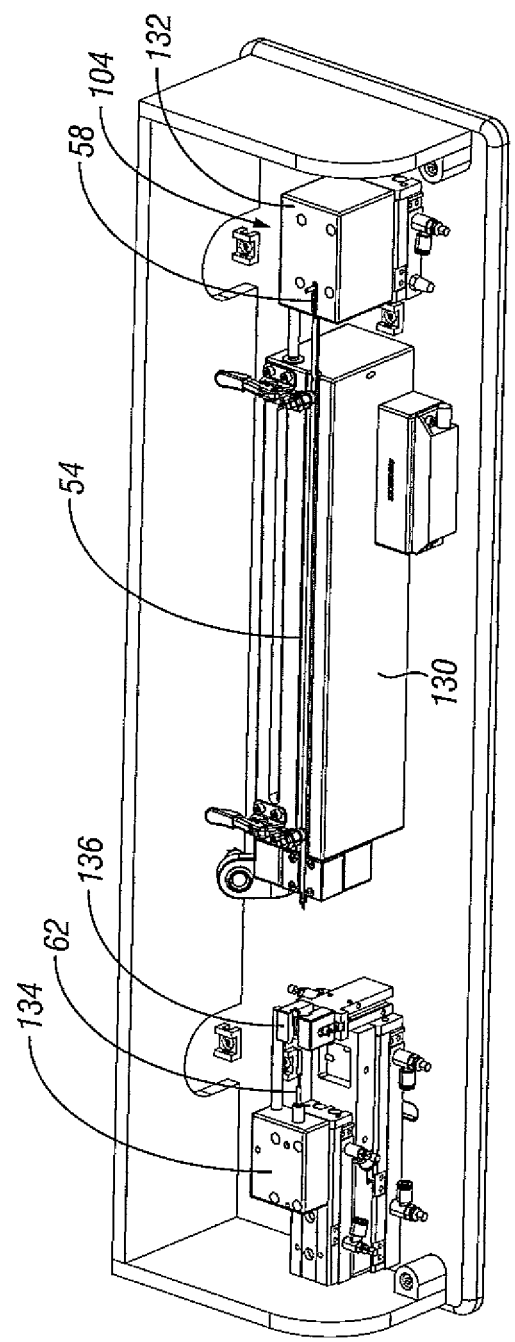
FIGS. 7A through 7C depict steps of the method summarized in FIG. 6 wherein components of the instrument including the knife and knife guide of FIG. 2A are manually loaded into the assembly device.
Figure 7B:
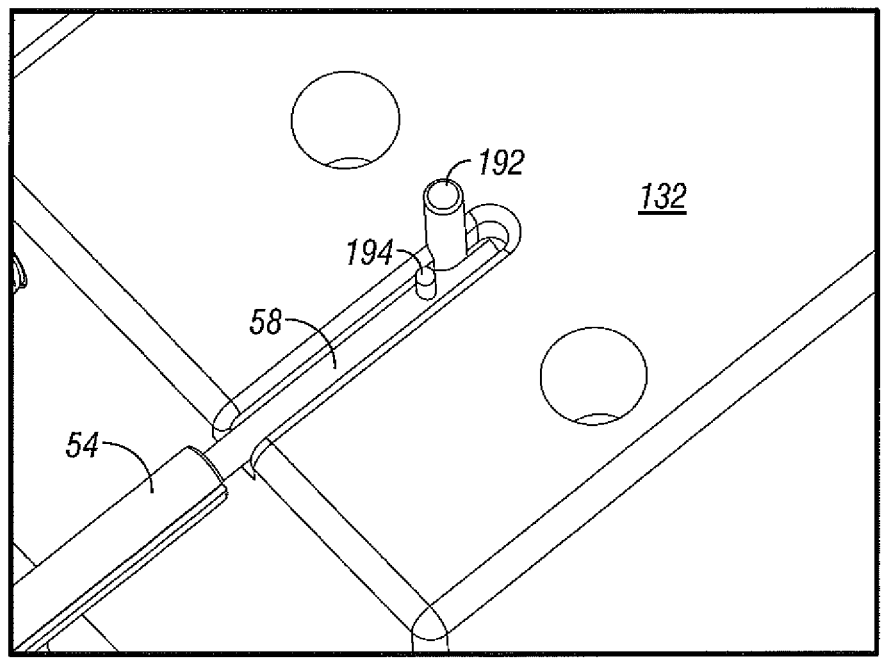

Once these components have been preassembled into a subassembly, they may be loaded into the assembly device 100. As depicted in FIG. 7A, the rotating shaft 54 is positioned to rest in the shaft reception channel 160 of fixture 130. Toggle clamps 162 are arranged to fix the position of the rotating shaft 54 relative to the stationary fixture 130. The knife bar 58 extends from rotating shaft 54 such that the rotating shaft 54 is separately restrained in knife block 132 as depicted in FIG. 7B. Knife block 132 includes a post 192 projecting there from to provide a locating and orienting mechanism for knife bar 58. Post 192 permits only a single orientation of knife bar 58 and thus ensures knife bar 58 is properly oriented. A locating pin 194 is installed through a prefabricated hole (visible in FIG. 2A) to fix the location of knife bar 58 relative to knife block 132. This arrangement provides for the reciprocation of knife bar 58 along with knife 42 within rotating shaft 54 at such time pneumatic slide 150 may be activated.

Figure 7C:
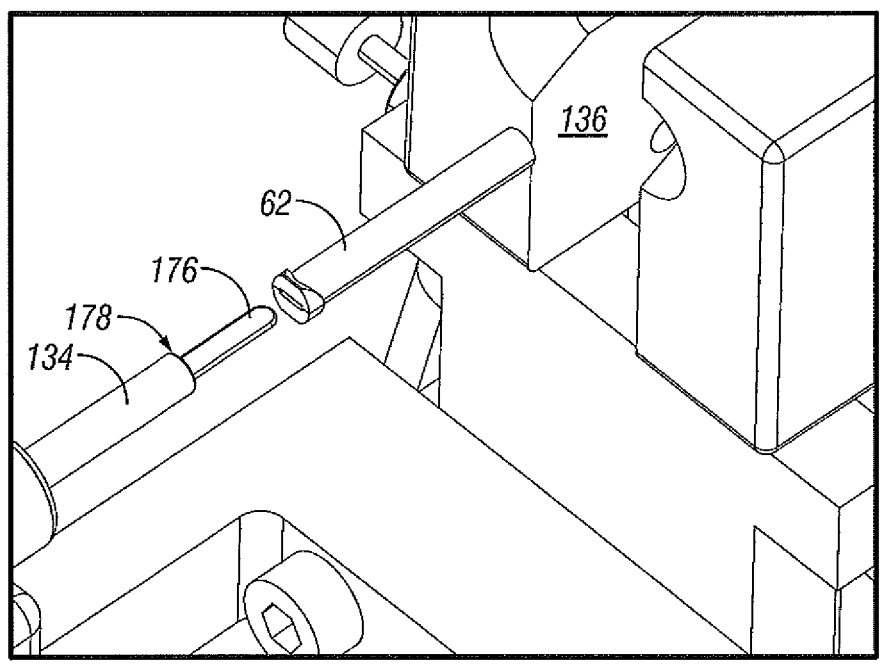

As depicted in FIG. 7C, knife guide 62 is loaded onto component block 134 before any automated movement occurs. Knife guide 62 is positioned onto the tongue 176 until the knife guide 62 abuts leading face 178. At this point, with rotating shaft 54, knife bar 58, knife 60, and knife guide 62 loaded into the assembly device 100, the safety cover 106 is closed and automated movement may be initiated.

Figure 8A:
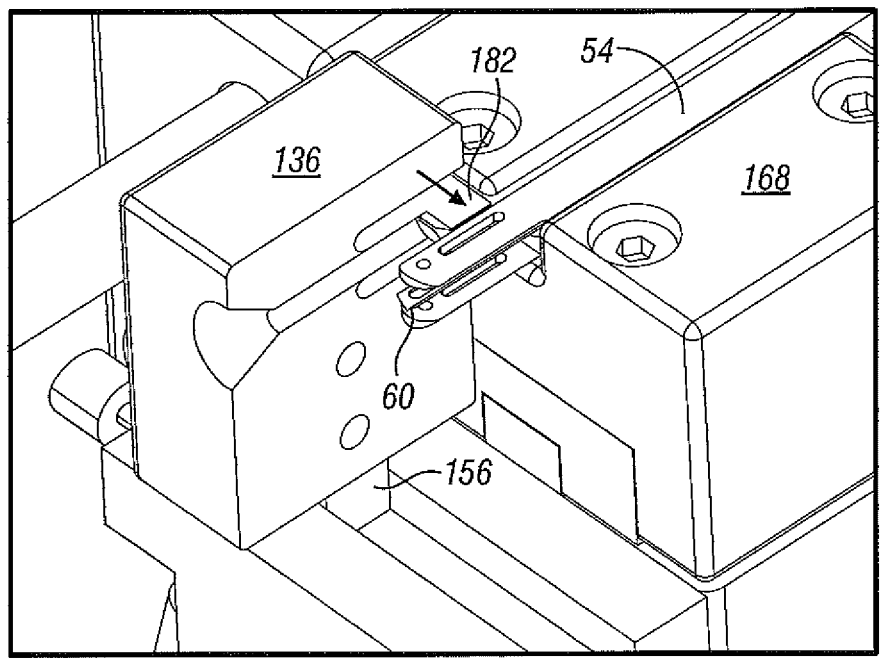
FIGS. 8A and 8B depict steps of the method wherein automated movement the assembly device constrains the knife.

Pneumatic slide 154 is initially activated or extended to deliver guide block 136 into proximity to fixture 130 and sensor housing 168 as depicted in FIG. 8A. Knife 60 projects into the bifurcated end of rotating shaft 54 due to the positioning of the proximal end of knife bar 58 in the knife block 132. Knife block 132 remains at a retracted or initial position thus defining the longitudinal position of the knife bar 58 and knife 60 within rotating shaft 54. The knife 60 may deviate from a central position between the two portions of the bifurcated end of the rotating shaft 54 due to blade variations, tolerance buildups, or other concerns. In particular, the knife 60 may be disposed off center in a vertical direction such that subsequent assembly of instrument components is complicated.

Figure 8B:
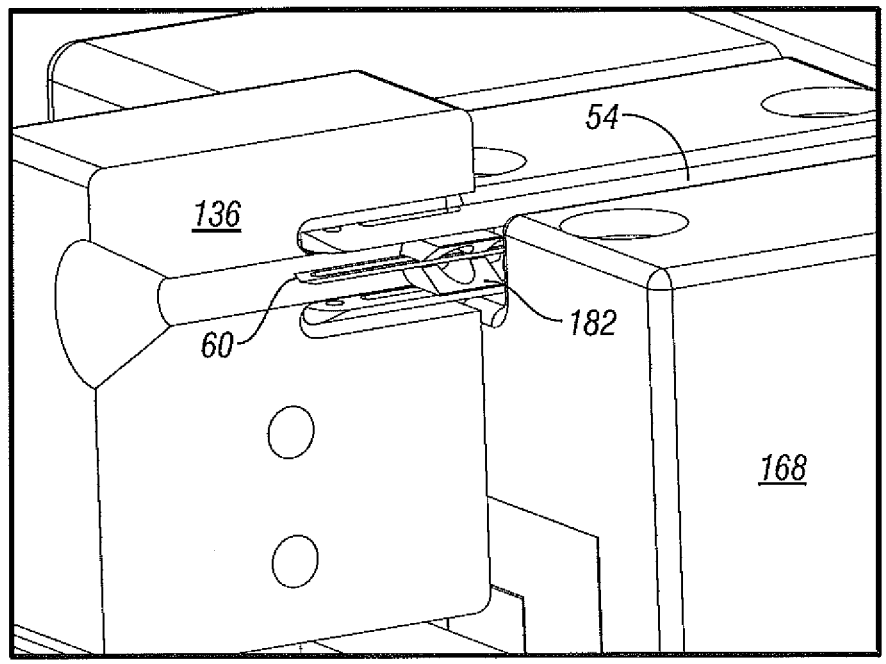

To ensure that the knife 60 is not damaged upon the assembly of subsequent instrument components, pneumatic slide 156 is activated to deliver guide block 136 from a retracted position to an extended position to restrain knife 60. As depicted in FIG. 8B, blade grip 182 on guide block 136 includes a pair of opposed tapered fingers with inclined surfaces that urge knife 60 into a central disposition as guide block 136 is extended in a lateral direction. A leading portion of the tapered fingers may encounter the knife 60 in an unrestrained position and a trailing portion of the tapered fingers may encounter the knife 60 in the restrained position. Thus a vertical position of knife 60 may be defined. Once knife 60 is centrally disposed, knife guide 62 may be safely constrained.

Figure 9A:
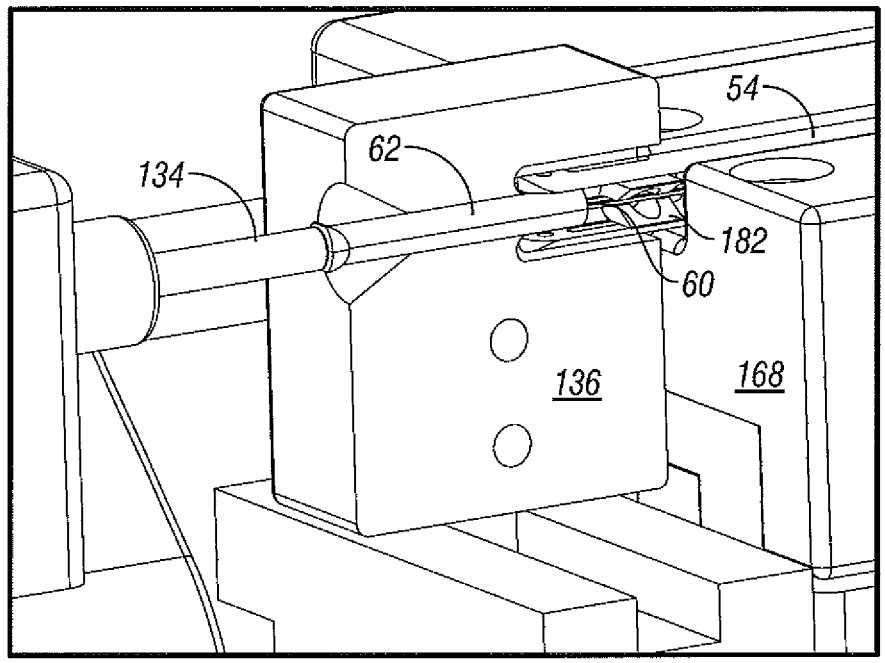
FIGS. 9A through 9D depict steps of the method wherein automated movement of the assembly device constrains and installs the knife guide.

Knife guide 62 is constrained by temporarily positioning the knife guide 62 between the two portions of the bifurcated end of rotating shaft 54 as depicted in FIG. 9A. Pneumatic slide 152 is activated and moved to a partially extended position to deliver the knife guide 62 to the bifurcated end of rotating shaft 54. Since the blade grip 182 maintains the knife 60 in a central disposition, the distal tip of the knife 60 avoids contact with the knife guide 182 and any damage resulting there from. Once constrained, knife guide 62 partially encloses a distal tip the knife 60.

Figure 9B:
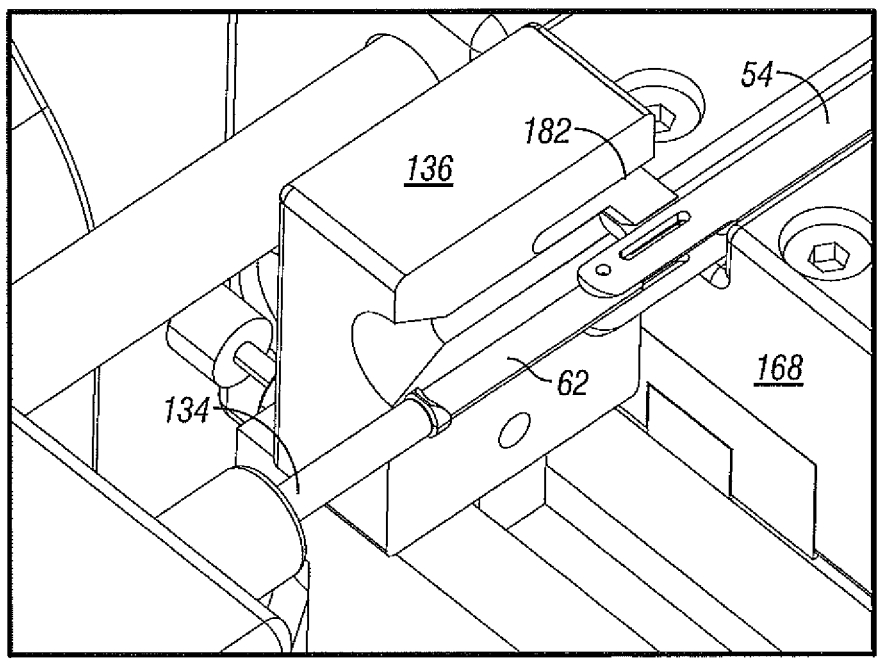
Figure 9C:
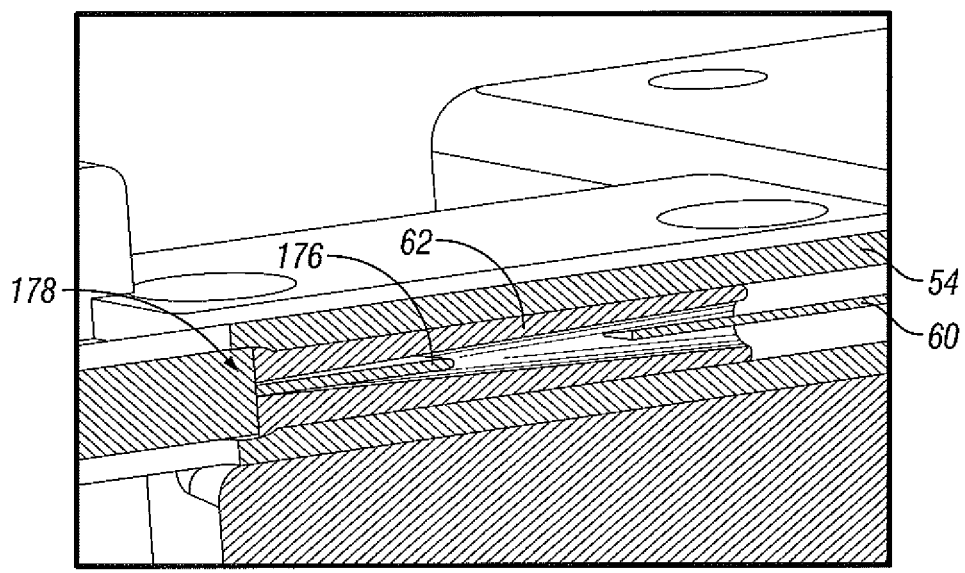

Next, pneumatic slide 156 is activated to return guide block 136 to a retracted position and release knife 60 from the blade grip 182 as depicted in FIG. 9B. With the knife 60 protected within knife guide 62, the knife guide 62 may be fully installed. Pneumatic slide 150 is extended concurrently with the further extension of pneumatic slide 152. The extension of pneumatic slide 150 will cause knife block 132 to draw knife bar 58 from rotating shaft in a proximal direction, and thus draw knife 60 in a proximal direction. The further extension of pneumatic slide 152 will move knife guide 62 proximally until knife guide 62 is pressed into position in rotating shaft 54. This concurrent movement may protect knife 60 from any damage that may result from contact with interior walls of knife guide 62. As depicted in FIG. 8C, the distal tip of knife 60 remains protected within the knife guide 62 throughout this assembly step.

Figure 9D:
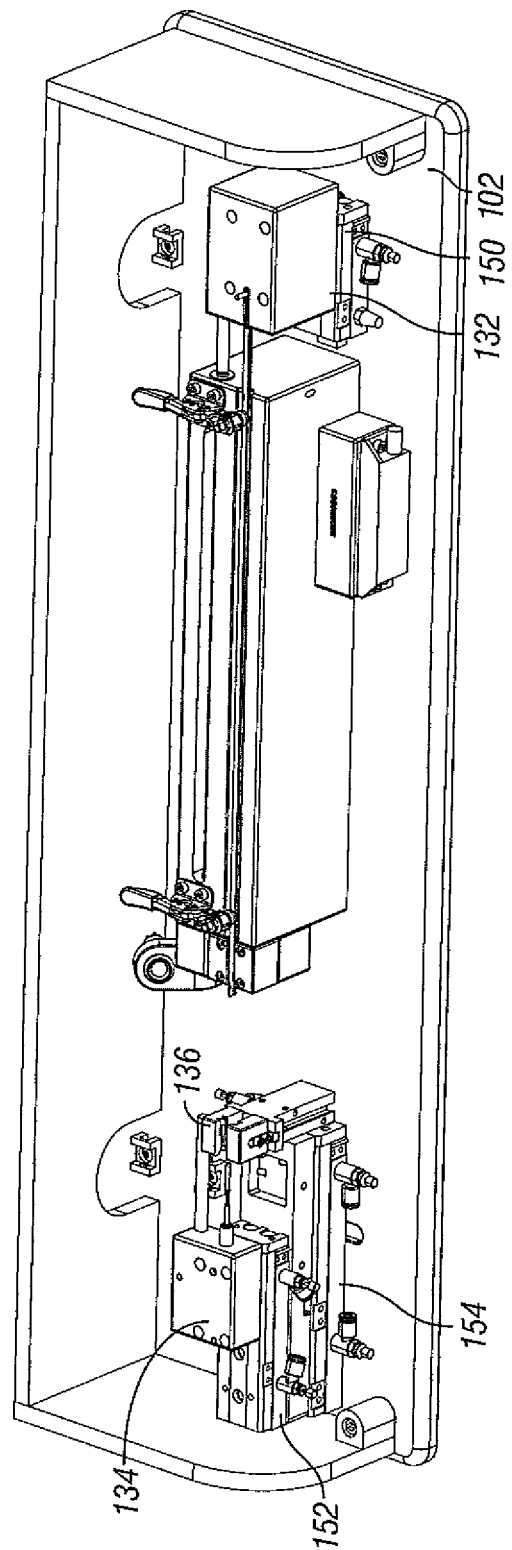

With knife guide 62 installed, pneumatic slides 152 and 154 are retracted returning 134 and 136 to their retracted positions. Pneumatic slide 150 remains extended as depicted in FIG. 9D such that knife block 132 remains in an extended position and knife 60 remains in a proximal position within knife guide 62 for the next assembly step.

Figure 10A:
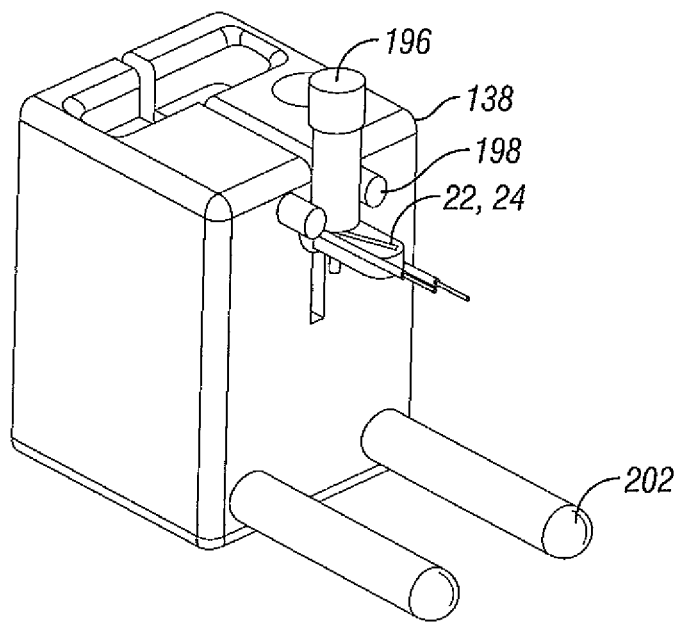
FIGS. 10A through 10C depict steps of the method wherein a pair of jaw members are assembled onto the instrument.

As depicted in FIG. 10A, jaw block 138 is manually loaded with jaw members 22, 24. A transfer pin 196 is positioned between two locating pegs 198 on jaw block 138 to locate and orient the jaw members 22, 24. Transfer pin 196 includes a lower pin portion configured to be received within pivot holes 76 or drive slots 78 in the proximal flanges 74 of jaw members 22, 24. When transfer pin 196 is installed, jaw members 22, 24 are properly arranged for assembly onto rotating shaft 54.

Figure 10B:
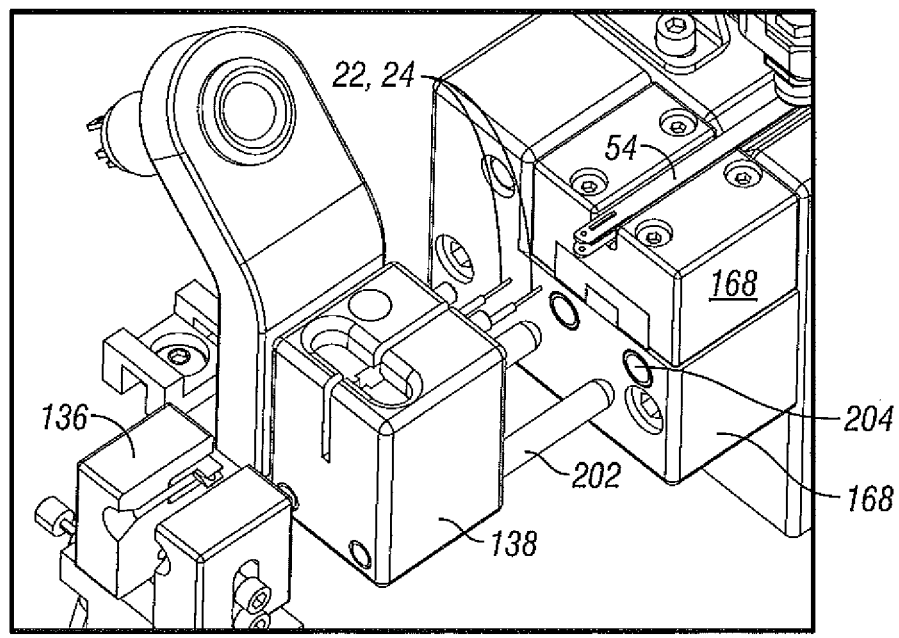

Safety cover 106 may be opened, and jaw block 138 pre-loaded with jaw members 22, 24 may be installed into the assembly device 100. As depicted in FIG. 10B, jaw block 138 includes a pair of locating prongs 202, which are received in a corresponding pair of holes in the sensor housing 168. Transfer pin 196 is removed prior to installation of jaw block 138 to allow proximal flanges 72, 74 of jaw members 22, 24 to be move between the two portions of the bifurcated distal end of rotating shaft 54.

Figure 10C:
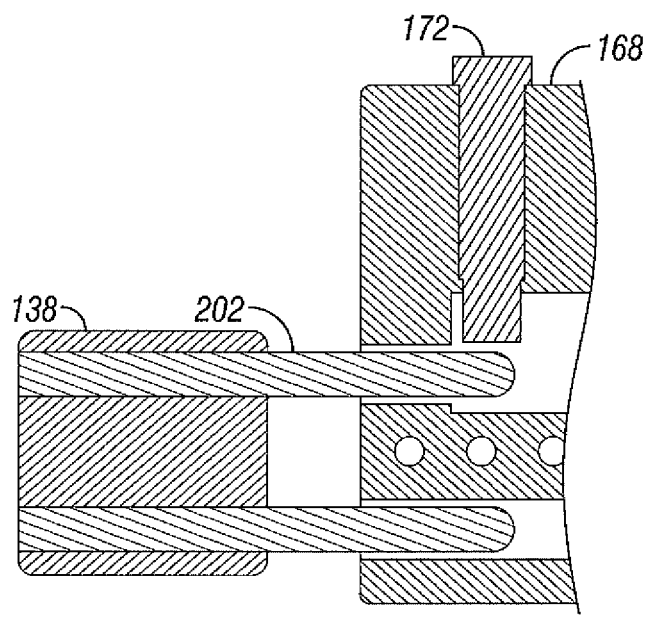

As depicted in FIG. 10C, sensor housing 168 includes a sensor such as proximity switch 172 configured to detect the presence of jaw block 138. When jaw block 138 is installed and proper alignment of the jaws, 22, 24 is confirmed, proximity sensor 172 sends an appropriate signal to the controller. When safety cover 106 is closed and the appropriate signal has been received, the controller permits pneumatic slide 150 to retract, thereby advancing knife bar 58 and knife 60 in a distal direction into jaw members 22, 24.

The knife 60 is advanced until the longitudinal slot 68 therein is situated between pivot holes 76 in the proximal flanges 72, 74 of the jaw members 22, 24. The safety cover 106 may then be opened, and transfer pin 196 is replaced. When replaced, transfer pin 196 is positioned through bore 84, or longitudinal slot 86 in the rotating shaft 54. As transfer pin 196 is replaced, the lower pin portion of transfer pin 196 will extend through the longitudinal slot 68 in the knife 60, thereby temporarily coupling the knife 60 to jaw members 22, 24.

This arrangement facilitates the manual installation of pivot pin 66 into pivot hole 84, and drive pin 68 into bore 80, thus capturing jaw members 22, 24 and knife 60. Manual installation of the boot 70 may complete the assembly of the distal portion of forceps 10. The distal portion is subsequently assembled with working head 28 to complete the forceps 10.

The process described above involves the use of pneumatic slides 150, 152, 154, and 156 to automate certain steps of the assembly process. Other automated actuators may be substituted for one, or any number of the pneumatic slides 150, 152, 154, and 156 such as servo or step motors. Alternatively, manually prompted movement is contemplated. For example, the step of restraining knife 60 within blade grip 182 may be accomplished manually. Guide block 136 may be configured to permit manual motion to slide blade grip 182 over knife 60. Control surface 190 may also be configured to facilitate any manual or semi-automatic movement.

Although the foregoing disclosure has been described in some detail by way of illustration and example, for purposes of clarity or understanding, it will be obvious that certain changes and modifications may be practiced within the scope of the appended claims.

What is claimed is:

1. A method of assembling a surgical instrument including a knife, the method comprising the sequential steps of:
   loading a subassembly of the surgical instrument that includes a knife into a fixture such that the knife is movable within the subassembly;
   advancing a blade grip to urge the knife to a restrained position within the subassembly;
   positioning a knife guide relative to the subassembly to constrain the knife guide within the subassembly; and
   moving the knife guide and the knife concurrently in a non-rotational manner in a first direction to install the knife guide.

2. The method of assembling a surgical instrument including a knife of claim 1, further comprising the step of:
   prior to the advancing step, closing a safety cover provided to protect an operator.

3. The method of assembling a surgical instrument including a knife of claim 2, further comprising the step of:
   providing a controller configured to permit automated movement when the safety cover is in a closed configuration, and disable automated movement when the safety cover is in an open configuration.

* * * * *